April 11, 1972 W. J. FLEMER ET AL Plant Pat. 3,108
ELM TREE
Filed Dec. 3, 1969
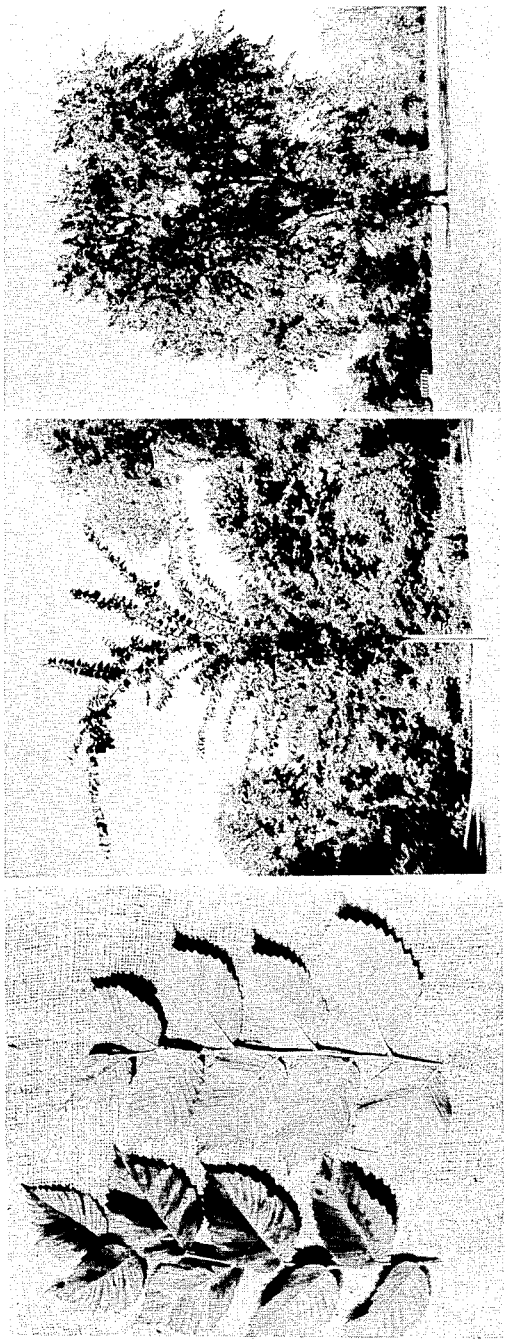
Inventors.
William Flemer, Jr.
William Flemer, III
By: Robbs & Robb
Attorneys.

United States Patent Office

Plant Pat. 3,108
Patented Apr. 11, 1972

3,108

ELM TREE

William J. Flemer and William Flemer III, Princeton, N.J., assignors to Treesearch, Kingston, N.J.

Filed Dec. 3, 1969, Ser. No. 881,942
Int. Cl. A01h *5/12*
U.S. Cl. Plt.—51 1 Claim

The present invention relates to a new and distinct variety of elm tree of the species botanically known as *Ulmus americana,* which was originated by us as a selected seedling derived from a large block of various nursery seedlings of unnamed and unpatented elm varieties of the American elm type, as planted and grown by us on our nursery property located in Plainsboro Township, N.J.

This particular seedling was initially selected by us as outstanding because of its superior form and superior rapidity of growth habit. It was then planted in a grove among other selected seedlings being grown on our nursery property aforesaid and kept under close observation. Some years later, the Dutch elm disease (*Ceratostomella ulmi*) invaded this grove and within two years time, all the trees died except the particular seedling referred to at the commencement hereof, although the trees of this grove had been planted closely enough for natural root grafts to have occurred with each other. The surviving tree was inoculated artificially with diseased elm bark patches during our continued observations and tests, but has remained remarkably free of the disease, with no evidence of the Dutch elm disease during our many years of observations and tests.

The continued and prolonged tests and observations for over 20 years of our new elm seedling and progeny thereof derived by bud graftings performed by us in our nursery aforesaid and also subjected to similar inoculations without resulting in infection of the trees of our new variety, even without spraying or other controls, when other varieties growing in the same area succumbed to Dutch elm disease, have demonstrated conclusively that the superior form, superior rapid growth habit and outstanding resistance to Dutch elm disease characteristics thereof are unique and come true and are established and transmitted through succeeding propagations. Otherwise, the characteristics are typical of the average American elm.

The accompanying drawing shows a typical young tree specimen of our new variety, at the age of about 5 years, and a typical mature tree, as well as typical leaf specimens on an enlarged scale and depicting both the upper and lower leaf surfaces.

The following is a detailed description of our new variety, with color terminology in accordance with the Munsell Color Chart, except where general color terms of ordinary dictionary significance are obvious, although no color factors are of distinctive significance:

Parentage: Selected seedling of an unnamed and unidentified variety of the species *Ulmus americana.*

Propagation: Holds its distinguishing characteristics through succeeding propagations by bud grafting.

Locality where grown and observed: Plainsboro Township, N.J.

Tree: Large; spreading; tall; hardy; rapid grower (about 20% faster than the average of ordinary American elm seedlings grown under the same conditions.

*Trunk.*—Stocky; rough.

*Branches.*—Slender; smooth. Color—Light Olive, Hue 5 Y 5/6. Lenticels—Moderately abundant.

Foliage:

*Leaves.*—Medium abundant; about 12 cm. long; about 8 cm. wide; cordate—acuminate; doubly serrate, with serrations about 1 cm. long and about 5 cm. deep.

Color—Upper surface—Moderate Olive Green, Hue 7.5 GY 4/4. Lower surface—Moderate Yellow Green, Hue 2.5 G Y 5/5. Fall color—Strong Orange Yellow.. Hue 10 Y R 7/10. Margin—Serrate. Petiole—Short. Glands—None. Stipules—Paired; about 1.5 cm. long; soon dropping as leaves mature.

Flower buds: No distinctive significance.

*Hardiness.*—Hardy to at least −20° F.

*Size.*—About 0.7 cm. long.

*Shape.*—Ovate; slightly flattened.

*Color.*—Medium brown.

Flowers:

*First bloom.*—About March 7 to 12.

*Full bloom.*—About March 12 to 16 in central New Jersey.

*Quantity.*—Sparse.

*Size.*—Small.

*Petalage.*—No significant distinctiveness.

Fruits: Ripen when born about May 10 to 14 in central New Jersey.

*Abundance.*—Moderately abundant.

*Size of wing.*—Length—About 1 cm. Width—About 0.75 cm. Color—Pale brown.

We claim:

1. A new and distinct variety of elm tree, substantially as herein shown and described, characterized particularly as to novelty by the unique combination of a general resemblance to typical American elms, but being particularly distinguished therefrom by a superior tree form, a superior and more rapid rate of growth, and a superior and outstanding resistance to Dutch elm disease.

No references cited.

ROBERT E. BAGWILL, Primary Examiner